United States Patent
Drasler et al.

(10) Patent No.: US 9,242,081 B2
(45) Date of Patent: Jan. 26, 2016

(54) POSITIONABLE VALVULOPLASTY CATHETER

(75) Inventors: William Drasler, Minnetonka, MN (US); Wesley Pedersen, Minneapolis, MN (US); Mark Ungs, Minnetonka, MN (US)

(73) Assignee: InterValve, Inc., Plymouth, MN (US)

( * ) Notice: Subject to any disclaimer, the term of this patent is extended or adjusted under 35 U.S.C. 154(b) by 262 days.

(21) Appl. No.: 13/231,807

(22) Filed: Sep. 13, 2011

(65) Prior Publication Data
US 2012/0083809 A1   Apr. 5, 2012

Related U.S. Application Data

(60) Provisional application No. 61/382,446, filed on Sep. 13, 2010.

(51) Int. Cl.
| A61M 31/00 | (2006.01) |
| A61B 5/00  | (2006.01) |
| A61M 29/02 | (2006.01) |
| A61M 25/10 | (2013.01) |

(52) U.S. Cl.
CPC ............ *A61M 29/02* (2013.01); *A61M 25/1002* (2013.01); *A61M 25/104* (2013.01); *A61M 2025/1059* (2013.01); *A61M 2025/1072* (2013.01); *A61M 2025/1084* (2013.01)

(58) Field of Classification Search
CPC .......... A61M 25/1002; A61M 25/104; A61M 2025/1084; A61M 2025/1059; A61M 2025/1072
See application file for complete search history.

(56) References Cited

U.S. PATENT DOCUMENTS

| 4,327,736 A | 5/1982  | Inoue |
| 4,328,811 A | 5/1982  | Fogarty |
| 4,572,186 A | 2/1986  | Gould et al. |
| 4,630,609 A | 12/1986 | Chin |
| 4,723,549 A | 2/1988  | Wholey et al. |
| 4,763,654 A | 8/1988  | Jang |
| 4,777,951 A | 10/1988 | Cribier et al. |
| 4,787,388 A | 11/1988 | Hofmann |
| 4,796,629 A | 1/1989  | Grayzel |
| 4,819,751 A | 4/1989  | Shimada et al. |
| 4,878,495 A | 11/1989 | Grayzel |
| 4,906,244 A | 3/1990  | Pinchuk et al. |
| 4,909,252 A | 3/1990  | Goldberger |

(Continued)

FOREIGN PATENT DOCUMENTS

| EP | 0344530 A1 | 12/1989 |
| EP | 0351734 A1 | 1/1990 |

(Continued)

OTHER PUBLICATIONS

WIPO, U.S. International Search Authority, International Search Report and Written Opinion mailed Jan. 5, 2012 in International Patent Application No. PCT/US2011/051457, 7 page.

(Continued)

*Primary Examiner* — Jonathan W Miles
*Assistant Examiner* — Todd J Scherbel
(74) *Attorney, Agent, or Firm* — Inskeep IP Group, Inc.

(57) ABSTRACT

In one embodiment, a balloon catheter is provided for use during annuloplasty. Preferably, the balloon includes a distal, noncompliant portion and a proximal semi-compliant portion which allows for sequential inflation, reliable positioning, and compliance measurement.

19 Claims, 7 Drawing Sheets

(56) References Cited

U.S. PATENT DOCUMENTS

| | | | |
|---|---|---|---|
| 4,927,412 A | 5/1990 | Menasche | |
| 4,938,676 A | 7/1990 | Jackowski et al. | |
| 4,986,830 A | 1/1991 | Owens et al. | |
| 5,017,325 A | 5/1991 | Jackowski et al. | |
| 5,037,392 A | 8/1991 | Hillstead | |
| 5,055,024 A | 10/1991 | Jackowski et al. | |
| 5,074,845 A | 12/1991 | Miraki et al. | |
| 5,108,415 A | 4/1992 | Pinchuk et al. | |
| 5,156,612 A | 10/1992 | Pinchuk et al. | |
| 5,171,299 A | 12/1992 | Heitzmann et al. | |
| 5,223,205 A | 6/1993 | Jackowski et al. | |
| 5,236,659 A | 8/1993 | Pinchuk et al. | |
| 5,250,070 A | 10/1993 | Parodi | |
| 5,275,169 A | 1/1994 | Afromowitz et al. | |
| 5,295,958 A | 3/1994 | Shturman | |
| 5,295,995 A | 3/1994 | Kleiman | |
| 5,304,197 A | 4/1994 | Pinchuk et al. | |
| 5,330,429 A | 7/1994 | Noguchi et al. | |
| 5,342,305 A | 8/1994 | Shonk | |
| 5,352,199 A | 10/1994 | Tower | |
| 5,356,591 A | 10/1994 | Pinchuk et al. | |
| 5,443,446 A | 8/1995 | Shturman | |
| 5,447,497 A | 9/1995 | Sogard et al. | |
| 5,449,371 A | 9/1995 | Pinchuk et al. | |
| 5,453,091 A | 9/1995 | Taylor et al. | |
| 5,470,313 A | 11/1995 | Crocker et al. | |
| 5,484,411 A | 1/1996 | Inderbitzen et al. | |
| 5,501,667 A | 3/1996 | Verduin, Jr. | |
| 5,545,209 A | 8/1996 | Roberts et al. | |
| 5,549,551 A | 8/1996 | Peacock, III et al. | |
| 5,647,847 A | 7/1997 | Lafontaine et al. | |
| 5,653,690 A | 8/1997 | Booth et al. | |
| 5,693,014 A | 12/1997 | Abele et al. | |
| 5,728,064 A | 3/1998 | Burns et al. | |
| 5,738,653 A | 4/1998 | Pinchuk et al. | |
| 5,752,522 A | 5/1998 | Murphy | |
| 5,792,300 A | 8/1998 | Inderbitzen et al. | |
| 5,795,325 A | 8/1998 | Valley et al. | |
| 5,797,877 A | 8/1998 | Hamilton et al. | |
| 5,843,116 A | 12/1998 | Crocker et al. | |
| 5,868,708 A | 2/1999 | Hart et al. | |
| 5,902,308 A | 5/1999 | Murphy | |
| 5,908,448 A | 6/1999 | Roberts et al. | |
| 5,947,924 A | 9/1999 | Liprie | |
| 5,961,536 A | 10/1999 | Mickley et al. | |
| 6,010,480 A | 1/2000 | Abele et al. | |
| 6,010,511 A | 1/2000 | Murphy | |
| 6,110,142 A | 8/2000 | Pinchuk et al. | |
| 6,136,258 A | 10/2000 | Wang et al. | |
| 6,190,354 B1 | 2/2001 | Sell et al. | |
| 6,210,338 B1 | 4/2001 | Afremov et al. | |
| 6,241,678 B1 | 6/2001 | Afremov et al. | |
| 6,267,747 B1 | 7/2001 | Samson et al. | |
| 6,296,660 B1 | 10/2001 | Roberts et al. | |
| 6,344,045 B1 | 2/2002 | Lim et al. | |
| 6,402,778 B2 | 6/2002 | Wang | |
| 6,409,741 B1 | 6/2002 | Crocker et al. | |
| 6,416,494 B1 | 7/2002 | Wilkins | |
| 6,488,653 B1 | 12/2002 | Lombardo | |
| 6,495,090 B1 | 12/2002 | Wilkins | |
| 6,500,146 B1 | 12/2002 | Pinchuk et al. | |
| 6,500,148 B1 | 12/2002 | Pinchuk et al. | |
| 6,511,469 B2 | 1/2003 | Ackerman et al. | |
| 6,537,247 B2 | 3/2003 | Shannon | |
| 6,544,224 B1 | 4/2003 | Steese-Bradley | |
| 6,562,056 B2 | 5/2003 | Jervis | |
| 6,565,589 B1 | 5/2003 | Jervis et al. | |
| 6,607,544 B1 | 8/2003 | Boucher et al. | |
| 6,607,545 B2 | 8/2003 | Kammerer et al. | |
| 6,626,861 B1 * | 9/2003 | Hart et al. | 604/96.01 |
| 6,632,196 B1 | 10/2003 | Houser | |
| 6,645,222 B1 | 11/2003 | Parodi et al. | |
| 6,663,647 B2 | 12/2003 | Reiley et al. | |
| 6,733,513 B2 | 5/2004 | Boyle et al. | |
| 6,896,842 B1 | 5/2005 | Hamilton et al. | |
| 6,942,680 B2 | 9/2005 | Grayzel et al. | |
| 7,229,403 B2 | 6/2007 | Schock et al. | |
| 7,309,324 B2 | 12/2007 | Hayes et al. | |
| 7,354,419 B2 | 4/2008 | Davies, Jr. et al. | |
| 7,618,432 B2 * | 11/2009 | Pedersen et al. | 606/194 |
| 7,744,620 B2 * | 6/2010 | Pedersen et al. | 606/194 |
| 7,951,111 B2 * | 5/2011 | Drasler et al. | 604/103.13 |
| 8,486,102 B2 * | 7/2013 | Pedersen et al. | 606/194 |
| 2001/0047163 A1 | 11/2001 | Samson et al. | |
| 2003/0028211 A1 | 2/2003 | Crocker et al. | |
| 2004/0073164 A1 | 4/2004 | Boatman et al. | |
| 2004/0093008 A1 | 5/2004 | Zamore | |
| 2005/0075662 A1 * | 4/2005 | Pedersen et al. | 606/194 |
| 2005/0090846 A1 * | 4/2005 | Pedersen et al. | 606/159 |
| 2005/0137621 A1 | 6/2005 | Stahl et al. | |
| 2006/0015133 A1 | 1/2006 | Grayzel et al. | |
| 2006/0016064 A1 | 1/2006 | Boatman et al. | |
| 2006/0085024 A1 | 4/2006 | Pepper et al. | |
| 2006/0135985 A1 * | 6/2006 | Cox et al. | 606/194 |
| 2007/0142771 A1 | 6/2007 | Durcan | |
| 2007/0213663 A1 | 9/2007 | Wang | |
| 2007/0213760 A1 | 9/2007 | Hayes et al. | |
| 2007/0219490 A1 | 9/2007 | Pepper et al. | |
| 2008/0009746 A1 | 1/2008 | Forster et al. | |
| 2008/0015687 A1 | 1/2008 | Lashinski et al. | |
| 2010/0022877 A1 | 1/2010 | Chono | |
| 2010/0094209 A1 * | 4/2010 | Drasler et al. | 604/95.04 |
| 2010/0228277 A1 * | 9/2010 | Pedersen et al. | 606/194 |
| 2011/0218564 A1 * | 9/2011 | Drasler et al. | 606/192 |
| 2011/0264201 A1 * | 10/2011 | Yeung et al. | 623/2.11 |

FOREIGN PATENT DOCUMENTS

| | | | |
|---|---|---|---|
| EP | 0419291 A1 | 3/1991 | |
| EP | 0669143 A1 | 8/1995 | |
| EP | 0829271 A1 | 3/1998 | |
| EP | 1062966 A1 | 12/2000 | |
| EP | 1352671 A1 | 10/2003 | |
| EP | 1352672 A2 | 10/2003 | |
| WO | WO 89/02763 A1 | 4/1989 | |
| WO | WO 91/01773 A1 | 2/1991 | |
| WO | WO 95/23625 A1 | 9/1995 | |
| WO | WO 99/15223 A1 | 4/1999 | |

OTHER PUBLICATIONS

WIPO, IB International Preliminary Examining Authority, International Preliminary Report on Patentability mailed Apr. 12, 2011 in International Patent Application No. PCT/US2009/060239, 8 pages.

WIPO, U.S. International Search Authority, International Search Report and Written Opinion mailed Feb. 5, 2010 in International Patent Application No. PCT/US2009/060239, 11 pages.

WIPO, U.S. International Preliminary Examining Authority, International Preliminary Report on Patentability mailed Apr. 18, 2006 in International Patent Application No. PCT/US2004/023251, 4 pages.

WIPO, U.S. International Search Authority, International Search Report and Written Opinion mailed Dec. 5, 2005 in International Patent Application No. PCT/US2004/023251, 6 pages.

Eisenhauer, Andrew C. et al., "Balloon Aortic Valvuloplasty Revisited: The Role of the Inoue Balloon and Transseptal Antegrade Approach," *Catheterization and Cardiovascular Interventions* 50:484-491, Aug. 2000, 8 pages.

* cited by examiner

POSITIONABLE VALVULOPLASTY CATHETER

RELATED APPLICATIONS

This application claims priority to U.S. Provisional Application Ser. No. 61/382,446 filed Sep. 13, 2010 entitled Positionable Valvuloplasty Catheter, which is hereby incorporated herein by reference.

BACKGROUND OF THE INVENTION

The following patents are hereby incorporated by reference in their entirety: U.S. Pat. Nos. 7,618,432; 7,744,620; and 7,951,111.

This invention is related to balloon catheters used for locating a position within a blood vessel or tubular member of the body, dilating tissue found within the tubular member, and measuring the compliance characteristics of tissue or the tubular member. Specifically, this device is intended for locating the balloon across the aortic annulus and aortic sinus, dilating the diseased aortic valve leaflets, and measuring the compliance characteristics of the annulus or sinus region.

Currently cylindrically shaped balloons are used to perform valvuloplasty procedures wherein the stenotic aortic valve leaflets are dilated or pushed back into the space of the aortic sinus. This procedure is typically performed under fluoroscopic guidance while the heart is beating. Movement of the heart, flow of blood, and inaccuracies in of fluoroscopic guidance do not always allow for accurate placement of the valvuloplasty catheter across the aortic annulus and sinus.

Recently dog-bone-shaped balloons have been presented (see U.S. Pat. No. 7,618,432) that provide for improved positioning across the aortic annulus and sinus. Also, dog-bone-shaped balloons have been presented that are able to measure the diameter of the aortic annulus as well as indicate the compliance characteristics of the aortic annulus (see U.S. Pat. No. 7,951,111).

Dilation of the aortic valve leaflets into the aortic sinus can cause the sinus to become overly distended and potentially encounter dissection or tearing which can result in patient death. Under current fluoroscopic visualization the physician does not know when the balloon has made contact with the leaflets, does not know if the aortic sinus is being overdistended, and he does not have information indicating the compliance characteristics of the aortic sinus or annulus. Such information would be useful to the clinician to ensure safety to the patient during dilation of the stenotic aortic valve leaflets to obviate annulus and sinus dissection and to ensure adequate dilation of the leaflets.

SUMMARY OF THE INVENTION

The present invention is a balloon catheter used for dilating tubular members of the body such as dilating stenotic aortic valve leaflets found in the aortic root. The balloon catheter has a balloon that is comprised of one region or portion that inflates earlier than the rest of the balloon to help position the balloon in the correct location within the tubular member. This portion of the balloon is made of a non-compliant (nc) material that is folded up during delivery and is unfolded as it is inflated at relatively low pressures. Another region or portion of the balloon is formed from a semi-compliant (sc) material or elastomeric material that undergoes expansion as pressure is increased within the balloon. Additionally, a waist region with a length that is larger than the aortic annulus and a diameter that is smaller than the aortic annulus and smaller than the bulb portion is located in either the nc portion or the sc portion.

For valvuloplasty applications the sc portion is inserted across the stenotic aortic valve leaflets while the nc portion is located in the left ventricular outflow tract (LVOT) upstream of the aortic annulus. A smaller diameter waist portion is located across the aortic annulus. Upon inflation to low pressures from zero to 0.5 atm the nc distal portion inflates first and allows the catheter to be pushed into place by the pulsating blood or pulled back proximally into position with the distal portion of the balloon located just upstream of the aortic annulus. Since it is sized larger than the valve annulus, the nc distal portion lodges itself in the valve region and prevents the balloon from being actively pushed via blood pressure and flow in a direction downstream toward the aorta. The sc proximal portion remains relatively small in diameter with only mild or no contact with the aortic valve leaflets thereby allowing the sc portion to be easily pulled further if needed through the opening provided by the stenotic aortic valve leaflets.

Upon further inflation from 0.1 to 2 atm, the sc proximal portion of the balloon contacts the stenotic leaflets and begins to push them outward against the aortic sinus. Balloon contact with the leaflets can be observed by noting an inflection point and an increase in the slope of the dP/dV curve that is higher than that normally observed for the dP/dV compliance curve for the sc portion of the balloon.

A computerized control system and display can be used to monitor the pressure versus volume slope and determine if a change in slope is occurring. The computer can detect an inflection point in the pressure-volume curve and can record the pressure at the time of the inflection as well as calculate slope changes. These calculations can then be used to determine the compliance of the tissues that are being contacted and expanded by the balloon. Further description of the computerized system is found in the US patent application by Drasler referenced earlier.

Further inflation of the balloon from 0.5 atm to higher than 2 atm causes the sc portion of the balloon to further dilate the leaflets outward. The stenotic leaflets can come into contact with the aortic sinus; this contact will be noted by an inflection point and an increase in the slope of the dP/dV curve. Observation of the slope of the dP/dV compliance curve following contact of the leaflets with the sinus reflects the compliance of the stenotic leaflets, the sinus, and the sc portion of the balloon. Subtraction of the balloon compliance allows the physician to assess the compliance of the aortic tissues and determine if further dilation is warranted. This subtraction can be accomplished automatically with the computer control system and the tissue compliance can be displayed on a monitor.

The balloon structure in one preferred embodiment can have a dogbone shape in its fully expanded conformation. The dogbone shape can provide an improved locking of the balloon on each side, upstream and downstream, of the annulus. Also, the dogbone shape can allow the stenotic leaflets to be dilated in a hyperextended manner while maintaining a lower dilation diametric magnitude for the annulus.

The waist of the dogbone-shaped balloon of the present invention can be formed from the nc material and attain a diameter that is approximately equal to or somewhat smaller than the annulus diameter. Alternately, the balloon waist can be formed from a sc material and expansion of the waist can allow it to come into contact with the annulus thereby providing compliance data from the slope of the dP/dV curve to also be indicative of the annulus diameter and compliance.

In yet another embodiment, the balloon of the present invention can be shaped such that it forms a generally cylindrical shape after it is fully inflated. In this embodiment, the nc distal portion is inflated first at lower pressures while the sc proximal portion resists expansion due to its elastomeric character. Further expansion at higher pressures from 0.2 atm to approximately 2 to 4 atm causes the sc proximal portion to expand out to its fully expanded conformation.

The present invention can include limiting fibers located in the proximal sc portion of the balloon. These limiting fibers are intended to limit the amount of expansion that the sc proximal portion of the balloon can expand. The expansion limitation can be in the diametric direction, the axial direction, or both. Such limiting fibers can be wrapped fibers such as an elastomeric monofilament material wrapped via a helical wind with a multi-filament non-compliant material. The limiting fibers are either bonded or attached to the sc proximal portion of the balloon.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1A:
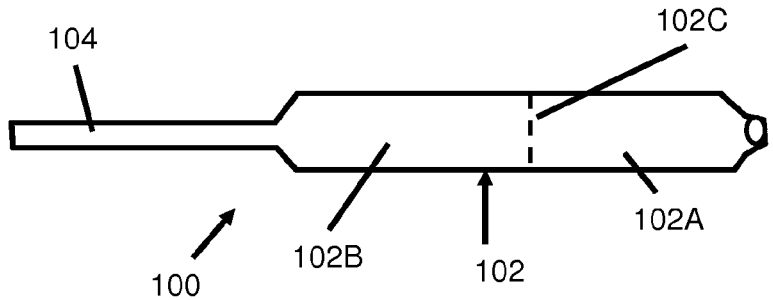
FIGS. 1A-1C illustrate an embodiment of a balloon catheter according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention includes a balloon dilatation catheter for positioning within a tubular vessel of the body and dilating a stenotic portion of the vessel. When used for valvuloplasty, the distal region or portion of the balloon is positioned in the left ventricular outflow tract and is inflated first to help position the balloon to a desirable location. The proximal region or portion of the balloon is positioned adjacent to the stenotic aortic valve leaflets such that they can be pushed back against the sinus. This dilation of the aortic valve leaflets can be accomplished as a stand-alone balloon aortic valvuloplasty (BAV) procedure or it can be performed as a pre-dilatation prior to implanting an aortic valve. The procedure can also be performed to dilate out other valves of the body or other stenotic regions of any tubular vessel of the body.

Figure 1B:
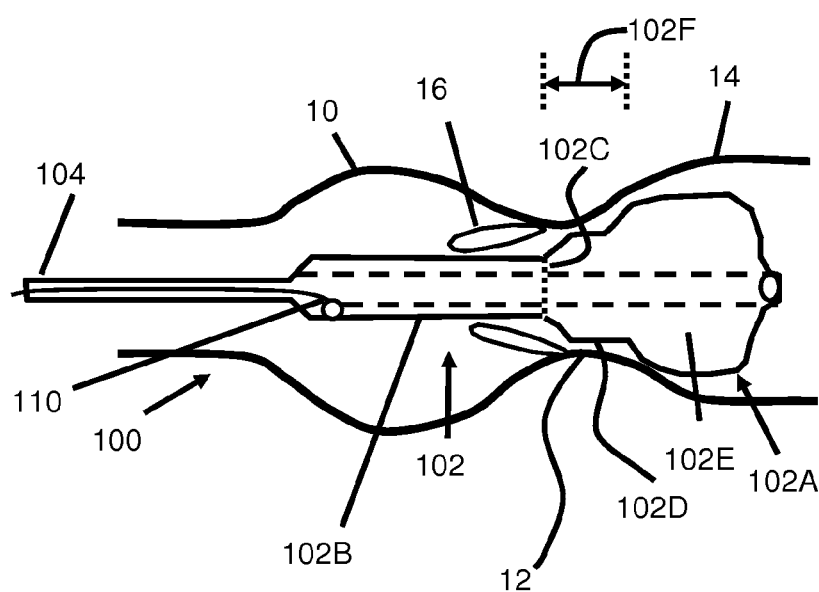
Figure 1C:
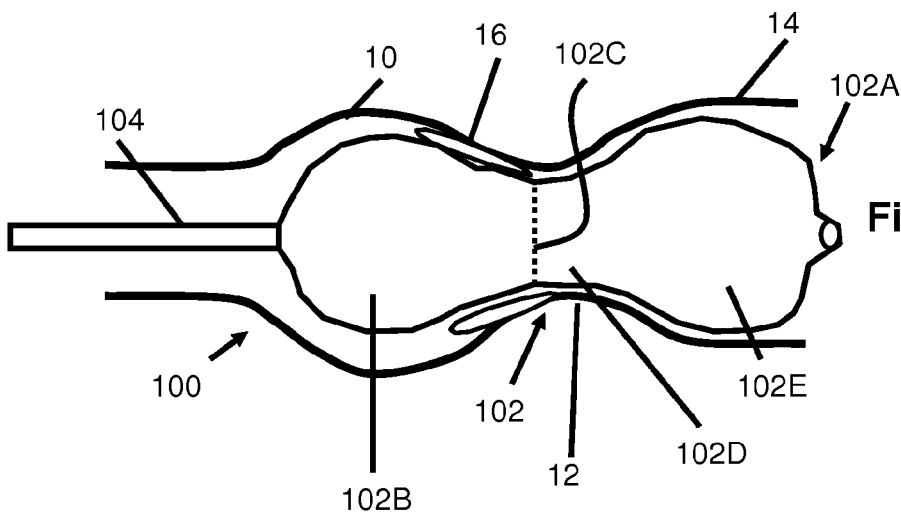

FIGS. 1A-1C illustrate a first embodiment of a dilatation device 100 according to the present invention. A balloon 102 is disposed at the distal end of a catheter shaft 104 and includes a distal non-compliant (nc) portion 102A and a proximal semi-compliant (sc) portion 102B. The sc portion 102B is joined to the nc portion 102A at a junction 102C located between the proximal end and the distal end of the balloon.

The balloon waist 102D of this embodiment is found in the distal nc portion 102A and extends from the junction 102C to the distal bulb 102E. Since the waist 102D and distal bulbous portion 102E are composed of nc material, they both will inflate earlier than the sc portion 102B. Further, even at relatively low pressures such as about 0.1-0.5 atmospheres the waist 102D and distal nc portion 102A can substantially attain their final diameter.

The length 102F of the waist 102D (including the angled, shoulder or transition region adjacent the junction 102C) in a preferred embodiment is about 4-10 mm (and can range from 2-15 mm). The nc balloon waist 102D ensues that the waist cannot grow during further balloon inflation and therefore will reduce accidental dissection of the aortic annulus. The diameter of the waist is preferably constructed to be about 1-3 mm smaller than the aortic annulus diameter (but may also range between zero to 10 mm smaller).

The sc portion 102B can be formed from polyurethane, silicone, lower durometer nylon, other thermoplastic elastomer, thermoset elastomer or material that can expand outwards to a larger diameter upon application of internal pressure. The nc portion 102A can be formed from polyethyleneterephthalate (PET), nylon, Pebax, or other polymeric material that does not expand appreciably upon application of internal pressure within the balloon.

The balloon 102 may include a sc polyurethane thermoplastic elastomer layer that extends throughout the entire proximal and distal portion. The nc portion 102A can be located as a second, outer layer at the distal portion of the balloon 102 while the proximal portion leaves the polyurethane layer exposed to allow for expansion. Hence, the balloon 102 can have a proximal portion that is compliant and a distal portion that is non-compliant.

This "layered" approach to creating the balloon 102 can be accomplished by coextruding a nc material over a sc material and ablating the nc material away from the portion of the balloon that is sc. Alternately, a separate nc balloon can be formed and a distal portion can be excised from it and bonded to the sc inner polyurethane layer located in the distal portion of the balloon. Other methods for forming the balloon are described in the U.S. Pat. Nos. 7,618,432; 7,744,620; and 7,951,111 which were previously incorporated by reference.

Figure 4A:
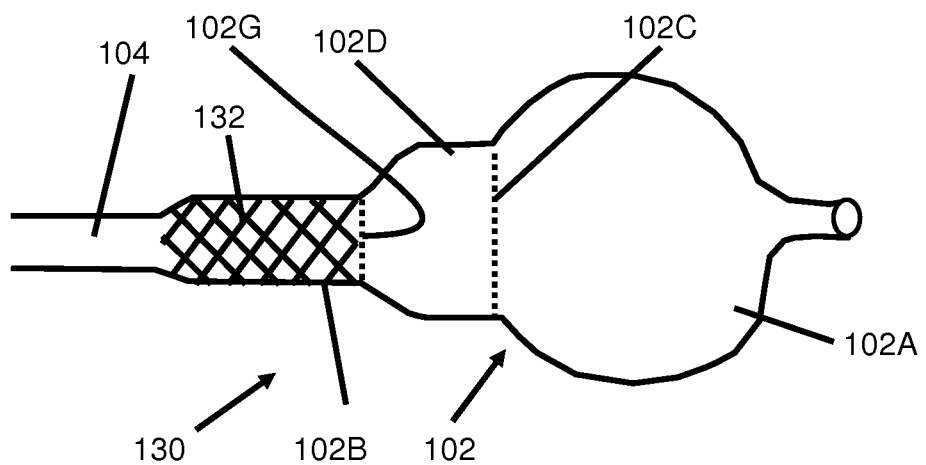
FIGS. 4A and 4B illustrate another embodiment of a balloon catheter according to the present invention.
Figure 4B:
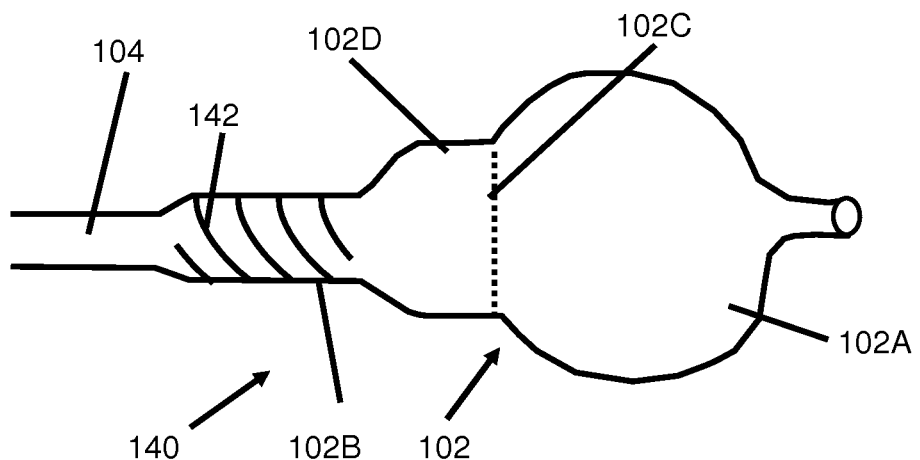

In one embodiment, the sc portion 102B can have a maximum inflation size that is limited by one or more embedded filaments or fibers. For example, the proximal sc portion 102B of the balloon 102 can have a layer of braided polymeric filaments 132 (seen on balloon 130 in FIG. 4A) or a layer of a helically wound polymeric filament 142 (seen on balloon 140 in FIG. 4B). The layers 132 or 142 can be embedded within the balloon wall or otherwise attached to the balloon wall. The polymeric filament is formed, in one example, from an internal core of polyurethane and wrapped with a spiral wrap of PET. This filament can be braided or wound onto the sc proximal balloon portion 102B as shown in FIGS. 4A and 4B.

These braids can also be included on the nc waist 102D which thereby restricts the fully expanded diameter of the waist region 102D to a desired size. In this regard, a braid that expands to a larger diameter may begin at junction 102G.

This support structure can also help to reduce the amount of length change encountered by the proximal portion as it is exposed to increasing pressures. The methods for providing such a braid or helical wind are described in more depth in the U.S. Pat. Nos. 7,618,432; 7,744,620; and 7,951,111 which were previously incorporated by reference.

The balloon catheter 100 is typically introduced into the femoral arterial vasculature and advanced such that the balloon 102 is positioned with its distal portion 102A located in the left ventricular outflow tract 14 (LVOT) as shown in FIG. 1B. Upon inflation to a relatively low pressure of about 0.1-1.0 atm (preferably about 0.2-0.5 atm) the distal portion 102A of the balloon 102 is expanded such that the bulbous distal portion 102A lodges just upstream of the aortic valve annulus 12 as the catheter shaft 104 is place under tension or gently pulled by the clinical operator. The junction 102C of this embodiment is preferably located at a position along the balloon length such that it positions just downstream of the annulus 12 during use.

The balloon waist 102D, which is also formed from nc material in this embodiment, can locate adjacent to the annulus as also shown in FIG. 1B. The waist portion 102D preferably has a diameter at the previously described low inflation pressure of approximately 18-22 mm (range from 16-26 mm) and the distal bulb portion 102E preferably has a diameter of 22-25 mm (range 20-30 mm). Generally, the waist 102D is smaller than the distal portion 102E by between about 1-8 mm and more preferably 2-6 mm.

At the previously described low inflation pressure, the proximal portion 102B of the balloon 102 expands to or remains mostly deflated to a relatively smaller diameter than the waist 102C and distal portion 102A. Preferably the diameter of proximal portion 102B has a diameter such that upon application of tension to the shaft, the proximal balloon portion will slide easily through the opening found between the stenotic aortic valve leaflets 16 and will allow the balloon 102 will come into position as shown in FIG. 1B. Typically, the flow area for blood through a stenotic aortic valve is equal to or larger than approximately 0.4 cm$^2$ and has a diameter of approximately 7 mm. The diameter of the proximal portion 102B of the balloon is preferably about 7 mm (range from about 5-18 mm) at a pressure between about 0.2-0.5 atm when it is being pulled back into position as just described.

The balloon catheter of the present invention can also be positioned via the venous system or trans-apically. In the apical approach, the catheter is introduced through a thoracotomy in the patient's chest and enters into the apex of the heart. With this apical approach, the balloon shaft extends from the balloon through the apex of the heart and therefore the nc portion 102A and the sc portion 102B are located in the reverse positions on the shaft as that of the device 100 in FIGS. 1A and 1B (used with a femoral approach). It is to be understood that the present invention is equally applicable to the apical, trans-venous or femoral approach, however, only the femoral approach will described hereafter.

Figure 5A:
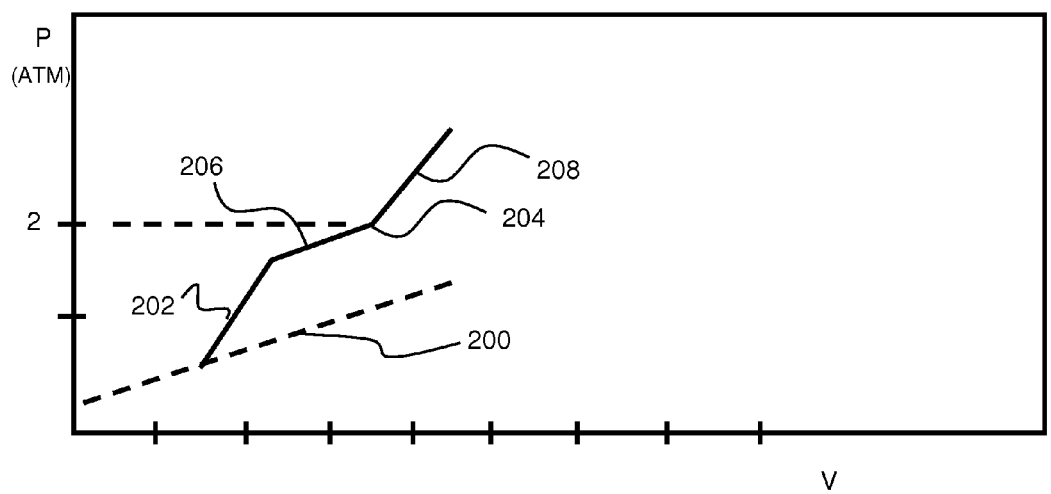
FIGS. 5A and 5B illustrate example pressure vs. volume graphs measured with regard to the balloon catheters of the present invention.

Upon positioning the balloon nc distal bulb portion 102E just upstream of the annulus, and the waist 102D across the aortic annulus, the pressure can be increased within the balloon to cause the sc proximal portion 102B to expand. The compliance of the sc proximal portion 102B generally follows a pressure-volume curve with a balloon compliance slope 200, dP/dV, that is associated with the modulus of the sc balloon material as shown in FIG. 5A. This dP/dV slope can be monitored by measuring the pressure via a pressure transducer 110 located in the balloon 102 (as seen FIG. 1B) or in fluid communication with the balloon (not shown). The change in balloon volume can be monitored by the amount of fluid delivered to the balloon via a delivery syringe that is connected to the balloon inflation lumen. Additional details relating to a system for monitoring balloon pressure and volume change can be found in U.S. Pat. Nos. 7,618,432; 7,744,620; and 7,951,111 which were previously incorporated by reference.

During a procedure, the inflated balloon 102 initially follows the balloon compliance slope 200, as seen in FIG. 5A. Contact of the proximal portion 102B of the balloon 102 with the stenotic leaflets 16 creates an increased slope of dP/dV, described here as the balloon/leaflet slope 202. This slope is higher than the balloon compliance slope 200 alone, due to additional resistance to expansion offered by the leaflets 16.

Continuing to inflate the balloon 102 can cause the leaflets 16 to fracture their fibrous and calcified structures and result in a drop in the slope of the balloon/leaflet compliance curve that may approach or be similar to the balloon compliance slope 200. This reduced slope is labeled as a balloon/fractured leaflet slope 206 in FIG. 5A.

Further inflation of the balloon 102 can cause the proximal sc portion 102B of the balloon to push the leaflets 16 outward into contact with the wall of the sinus 10 as shown in FIG. 1C. Upon contact with the sinus wall 10, an inflection point 204 is observed in the slope of the balloon/leaflet curve as the slope increases. This increased slope is described as the balloon/leaflet/sinus slope 208 and shown in FIG. 5A. The leaflets generally achieve desirable fractures when they are forced into intimate contact with the wall of the aortic sinus as shown in FIG. 1C and therefore, slope 208 may indicate to the user that this desirable expansion has occurred. In the embodiments of this specification, this contact may occur, for example above approximately 2 atm of pressure inside the balloon 102.

Provided that the leaflets have been significantly fractured, the balloon/leaflet/sinus slope 208 provides valuable information regarding the compliance of the sinus region. If the slope continues to increase above the balloon/leaflet slope, then the clinical operator knows that contact has been made with the sinus and obtains information regarding the compliance of the sinus 10.

The proximal sc portion 102B of the balloon 102 expands to a diameter that is larger than the diameter of the waist portion 102D, preferably ranging from 20-26 mm. This larger diameter for the sc proximal portion 102B may provide an improved hyperextension for the aortic valve leaflets 16 and also may help to lock the balloon 102 in a desirable position on each side of the annulus 12.

Figure 5B:
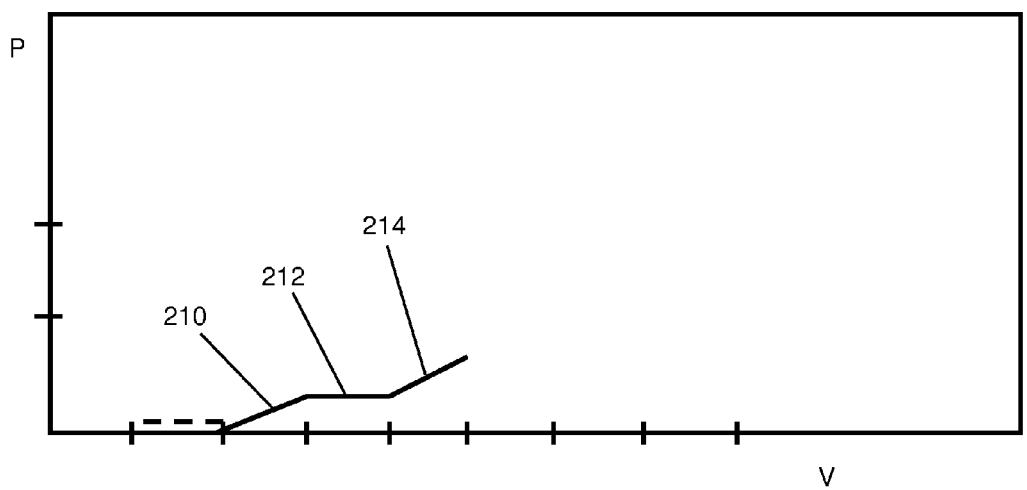

Assessment of the compliance of the leaflets and the leaflets/sinus can be obtained by subtracting the balloon compliance slope 200 (i.e., the compliance slope of the balloon alone in FIG. 5A) from the compliance of the balloon/leaflet slope 202 or the compliance of the balloon/leaflet/sinus slope 208. This balloon compliance slope 200 "subtraction" can be seen in the dP/dV curve of FIG. 5B, which shows the un-fractured leaflet compliance slope 210, the fractured leaflet compliance slope 212, and the leaflet/sinus compliance slope 214. The compliance of the leaflets can change as the fibrous tissues become fractured. The compliance of the leaflets/sinus can help the clinical operator to ensure safety to the patient by discontinuing dilation if the sinus tissue appears to be weak or beginning to fracture.

Figure 2A:
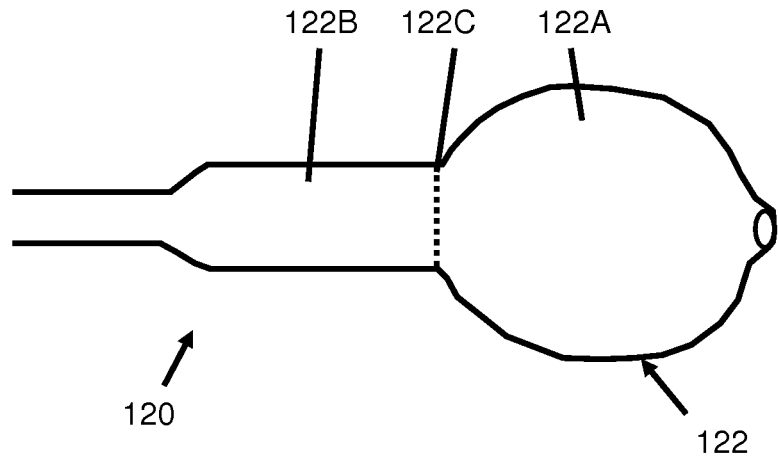
FIGS. 2A and 2B illustrate another embodiment of a balloon catheter according to the present invention.
Figure 2B:
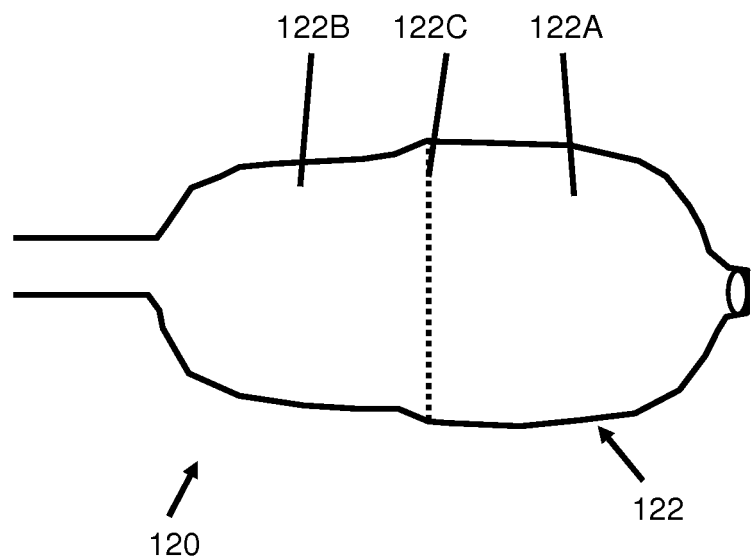

FIGS. 2A and 2B illustrate another embodiment of a balloon catheter 120 similar to that described in FIGS. 1A-1C having a balloon 122 with a nc distal portion 122A, a sc proximal portion 122B, and an interface 122C between the sc and nc portions of the balloon. However, when fully expanded, the balloon 120 achieves a generally stepped-shaped balloon (FIG. 2B).

As shown in FIG. 2A, the distal nc portion 122A of the balloon 122 inflates first at relatively low pressures to help position the nc distal portion of the balloon 122 just upstream of the annulus 12 in the LVOT as described with regard to the device 100. The balloon 122 is pulled back by the clinical operator such that the proximal sc portion 122B slides easily through the opening formed by the stenotic aortic valve leaflets 16 and across the aortic annulus. Upon further inflation as shown in FIG. 2B, the proximal sc portion 122B expands outwards to form a generally cylindrical shape with a diameter that is similar to that found crossing the annulus. Preferably, the balloon diameter adjacent to the annulus is approximately 20-23 mm (range 18-26 mm). The diameter of the nc distal portion 122A is preferably slightly larger, such as between about 22-28 mm (however a range of 20-30 is also possible).

Figure 3A:
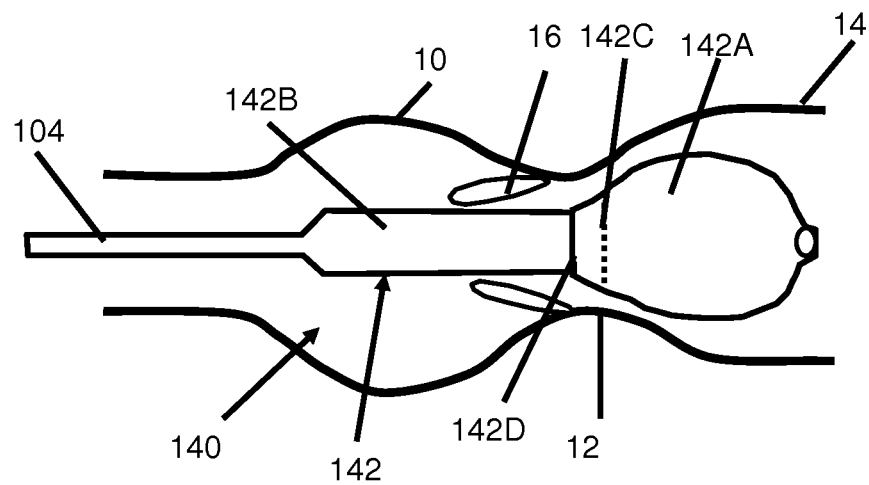
FIGS. 3A and 3B illustrate another embodiment of a balloon catheter according to the present invention.
Figure 3B:
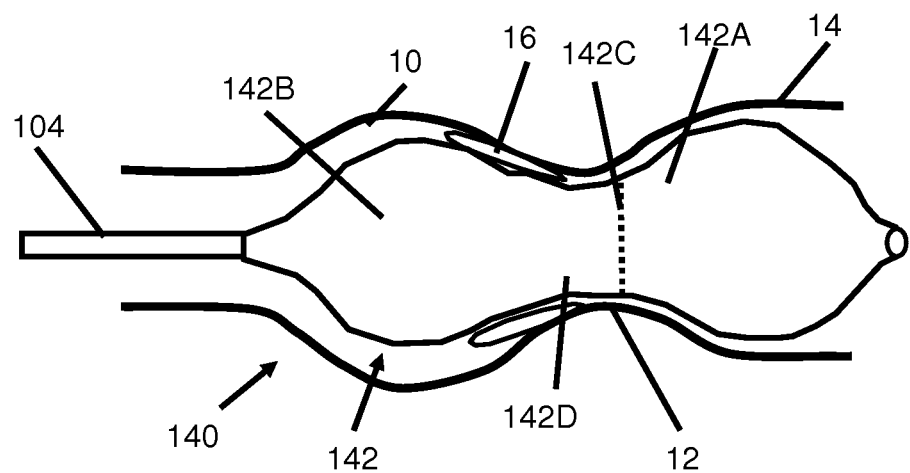

FIGS. 3A and 3B illustrate another embodiment of a balloon catheter 140 that is generally similar to the previously described embodiments, including a balloon 142, having a distal nc portion 142A, a proximial sc portion 142B, a junction interface 142C between the two portions 142A, 142B, and a narrowed waist portion 142D.

In this embodiment, the junction 142C is located such that it is positioned upstream of the annulus 12 (i.e. positioned upstream relative to the previously described embodiments). The waist 142D is included in the proximal sc region 142B.

In use, increasing pressure inflates the distal nc region 142A, similar to that described in the earlier embodiments and causes the balloon 142 to position just upstream of the annulus in the LVOT 14. Upon placing the shaft 104 under tension, the proximal sc region 142B is pulled through the stenotic aortic valve opening and the aortic annulus.

Upon further inflation to higher pressures, the proximal sc region 142B expands into contact with the leaflets 16 and an inflection point is noted as the slope increases to a balloon/leaflet slope 202 of the dP/dV curve, as described with regard to FIG. 5A. Further inflation pushes the leaflets 16 back towards the aortic sinus 10 until the leaflets 16 crack or fracture (slope 206) and also extends the waist portion 142D out into contact with the annulus 12. Contact of the leaflets with the aortic sinus 10 or contact of the balloon with the annulus 12 increase in the slope of the dP/dV curve (balloon/leaflet/sinus), creating another inflection point. This increased slope can be indicative of the compliance of the aortic sinus 10 or the annulus 12 or both as described earlier with regard to FIG. 5A. For this embodiment, the slope of the balloon/leaflet/sinus compliance curve 208 could also be reflective of the annulus compliance, since the proximal sc balloon portion 142B and the waist 142D can both make contact with the leaflets 16 and the annulus 12 respectively.

Preferably, this balloon 142 maintains a bulbous shape in its fully expanded configuration with the waist 142D ranging between about 1-5 mm smaller in diameter than either the proximal bulb 142B or the distal bulb 142A. The proximal and distal bulbs preferably have a diameter that ranges between about 21-28 mm. The waist length extends axially from about 4-10 mm (range 2-15 mm).

Figure 6A:
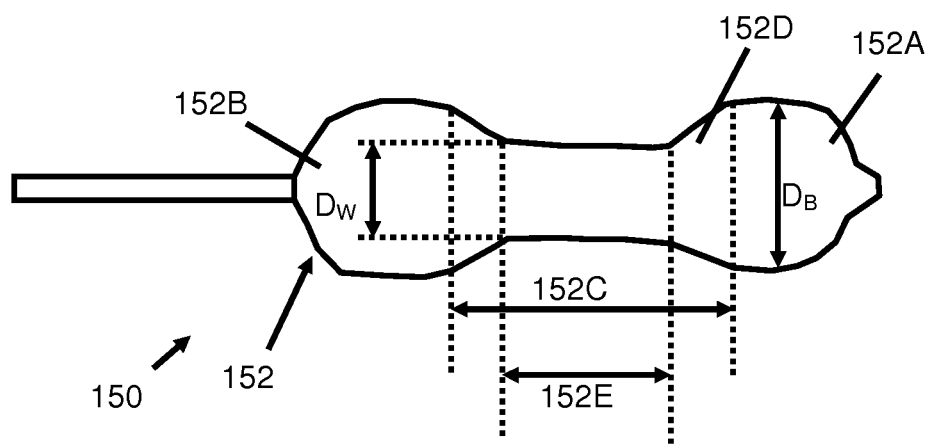
FIGS. 6A and 6B illustrate another embodiment of a balloon catheter according to the present invention.
Figure 6B:
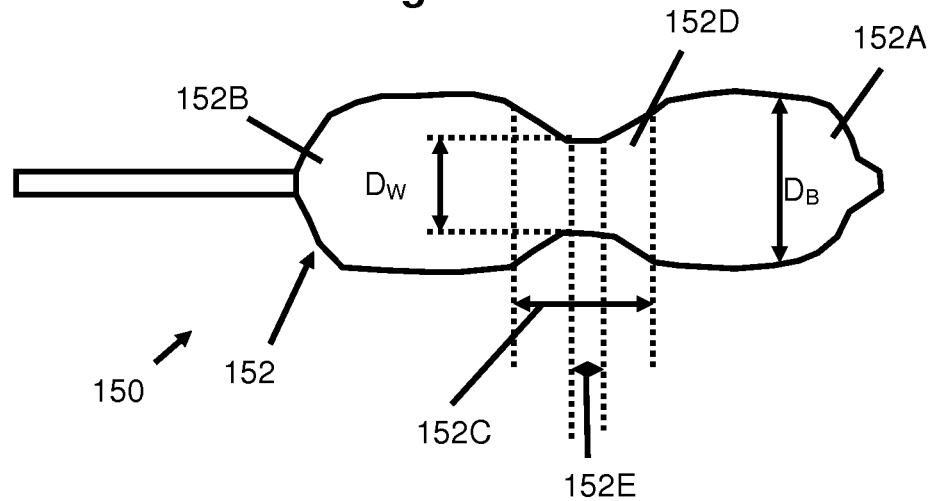

Another embodiment of a balloon catheter 150 is shown inflated to an initial, relatively low pressure (e.g., between about 0-0.5 atm) in FIG. 6A and inflated to a final, higher pressure (e.g., between about 1-4 atm) in FIG. 6B. The balloon 152 has two bulbs or bulb regions 152A, 152B located on each end of a waist region 152C. The waist or waist region 152C can be considered the combination of the central waist 152E plus the bevel regions 152D. Two bevels or bevel regions 152D connect each of the bulbs 152A, 152B with the central waist region 152E.

When the balloon 152 is fully expanded, the diameter of each bulb, $D_B$, is preferably about 24-30 mm and the diameter of the central waist 152E, $D_W$, is preferably about 15-24 mm. The bulb diameter ranges from 2-10 mm larger than the central waist diameter. The waist length is about 5-15 mm in this initial, low pressure state (about 0.1-0.5 atm.).

As seen in FIG. 6B, increased pressure and expansion of the balloon 152 causes the waist region 152C (i.e., the waist region 152E and/or beveled regions 152D) become shorter in length. In its initial configuration shown in FIG. 6A, the balloon 152 has a relatively long length of its central waist 152C that extends from the outer edge of the beveled region 152D on one side of the balloon 152 to the outer edge of the beveled region 152D on the other side. As the balloon 152 is expanded under pressure to its final configuration as shown in FIG. 6B, the length of the waist 152C extends a shorter distance from the outer ends of the beveled regions 152D. The waist length at pressures ranging from 1-4 atm is approximately 4-10 mm (range 2-12 mm).

This shortening of waist region 152C provides an advantage over other balloons by allowing the longer waist to be placed more easily across the aortic annulus 12 and across the stenotic leaflets 16 prior to full inflation of the balloon 152. Upon inflating the balloon to its final configuration, the waist will reduce in length to position the distal bulb region 152A against the upstream side of the annulus 12 and the proximal bulb 152B to push the leaflets 16 outwards against the wall of the aortic sinus 10. Thus the larger waist length is more easily positioned and properly located across the annulus 12, preventing the annulus 12 from being accidentally expanded by either of the bulbs 152A, 152B or exposed to any significant forces that could cause tearing or dissection. Also, the shortening of the length of the waist 152C can open the stenotic leaflets 16 more efficiently by providing an expansion force by the bulb region 152B that is directed at the outflow ends of the valve leaflets 16 to initiate leaflet opening. This action of opening leaflets 16 at the outflow ends provides a more consistent separation of the leaflets 16 that has particular benefit to opening stenotic bileaflet valves without as much potential for causing leaflet avulsion.

The diameter of the central waist region 152C, $D_W$, can remain approximately the same diameter from its initial to final configuration during inflation of the balloon 152. Alternately, an increase in central waist diameter within a predetermined range may also occur. Preferably, this central waist diameter range is approximately 2-6 mm smaller than the diameter of the bulbs 152A, 152B and smaller than the diameter of the annulus 12.

Preferably, the bulb diameter remains approximately the same diameter between its initial to final configuration although some diameter growth can be generally expected depending upon the material of construction. For example, a nylon balloon bulb material may grow in diameter by approximately 5-15% and a PET balloon bulb material may grow in diameter from 3-10% depending upon its wall thickness and processing conditions. Other typical medical device balloon materials are also contemplated including other generally noncompliant materials such as pebax, polyethylene, and others commonly used in the industry or semi-compliant (sc) materials including polyurethanes, silicones, lower durometer nylons, pebax, and copolymers of such materials.

The manufacture of this balloon 152 can be accomplished using a single material for the entire balloon, two or more balloon materials such as an inner balloon of one material and an outer balloon of another material, or a portion of one balloon inside or outside of another balloon material. For example, a nc material such as PET can be formed with a bulbous shape; the bulbous ends can be excised from the balloon and bonded over the bulbous ends of a balloon formed from a sc material such as nylon or polyurethane. Such balloon construction can include bonding or thermal forming or attachment of one balloon portion or region around another balloon portion or region, or balloon fabrication can include a coextrusion of two or more different materials that are then formed into a balloon. Further, the balloon or a portion of the balloon can be formed with a braided structure either bonded to or embedded within a portion of the balloon wall or the entire balloon wall.

In one example construction, plastic tubing can be extruded and blown into a balloon with a diameter similar to that of the desired central waist diameter. Preferably, this balloon attains a molecular circumferential orientation and a diameter that is smaller than the diameter of an aortic annulus 12. The blown balloon is then placed into a bulbous mold and the end regions or bulb regions are heated or annealed to allow molecular rearrangement. The central waist region can be cooled to ensure that the central waist will retain its circumferential molecular alignment. Upon further inflation of the balloon into the bulbous mold the bulb regions can regain molecular circumferential orientation to retain the large bulb diameter. It is noted that this construction method can be also used to form a bulbous or hour-glass shaped balloon out of a single polymeric material such that the waist will retain a smaller diameter and will not expand outwards to the diameter of the larger bulb diameters as the internal pressure is increased up to approximately 3-5 atmospheres. The polymeric material can be, for example, PET, nylon, pebax, or other nc or sc material that is suitable for forming such a balloon. Cooling temperatures and heating temperatures will vary according to the melting temperature and glass transition temperatures for these materials.

The beveled regions may require less orientation because they have not been expanded out to as large of a diameter. Also, thermal annealing of the beveled regions can be greater than that of the bulb regions, if necessary, to provide enhanced bevel growth under pressure. These bevel regions may then have a tendency during use, to grow to a relatively larger diameter than the central waist region when the pressure is increased. A portion of the bevel region can grow to a diameter that is equivalent or nearly equal to the diameter of a bulb region. This increase in diameter of the bevel regions then causes the waist length to reduce during balloon inflation and safely dilate the aortic valve leaflets with proper positioning of the bulbs on each side of the annulus, with more efficient dilation of the aortic valve leaflets, and without causing dilation to the annulus.

Figure 7A:
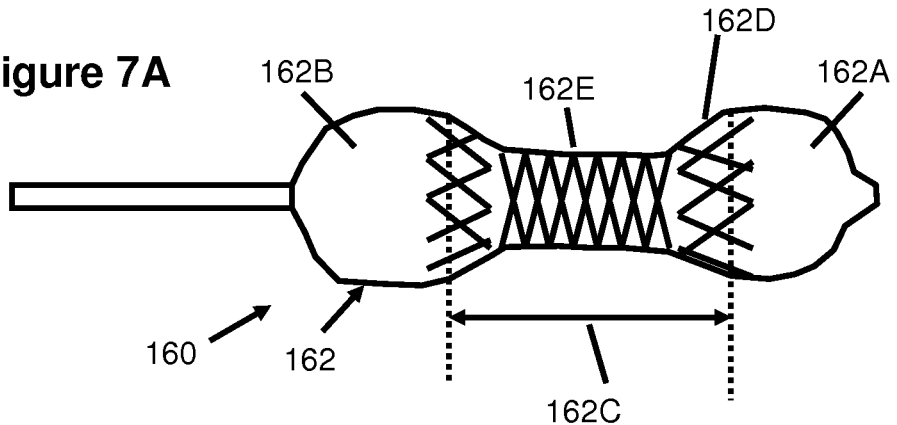
FIGS. 7A-7C illustrate another embodiment of a balloon catheter according to the present invention.
Figure 7B:
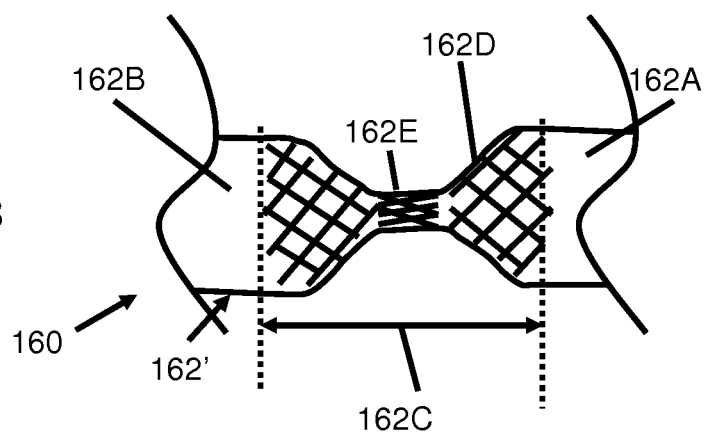
Figure 7C:
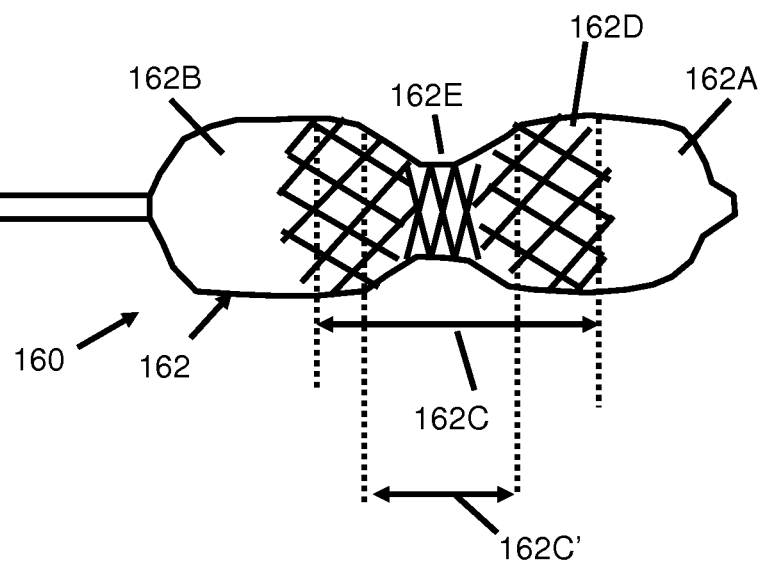

Yet other embodiments for constructing a balloon catheter 160 with a "shrinking" waist are shown in FIGS. 7A-7C. Specifically, FIGS. 7A and 7B illustrate two alternate configurations of a balloon 162 at a relatively low pressure, while FIG. 7C illustrates the balloon 162 at a relatively higher pressure. The expansion of the central waist 162C (including central waist 162E and beveled regions 162D) are controlled or limited by the inclusion of braided fibers. Depending on several characteristics of the braid, expansion is limited.

In FIG. 7A, the central waist 162C is preferably constructed out of either a semi-compliant (sc) material or a noncompliant (nc) material. A braid (i.e., braided fiber elements) are attached or embedded and preferably oriented the circumferential direction. In one example, the braid fiber angle with respect to the longitudinal axis of the balloon is about 75-85 degrees. The braid size, angle, material and orientation prevents the central waist 162E from becoming equal to or larger than the annulus diameter.

Alternately, a spiral winding of noncompliant fiber, such as Dacron, can be attached or embedded to the central waist 162E to prevent diametric expansion. In this alternate construction, the central waist 162 can be folded (if composed of nc material) to attain a low profile as require for delivery of the balloon into the tubular vessel or access site into the body.

The diameter of the central waist 162E and the central waist braid angle in one embodiment is preferably similar in its initial, relatively low pressure configuration (e.g., FIG. 7A or 7B) to that in the final higher pressure configuration (FIG. 7C). The bevel region 162D is preferably formed from a semi-compliant material with a bevel braid angle that is more axially directed than the central waist braid angle in the initial configuration. For example, the bevel braid angle is between about 45-75 degrees with respect to the axial direction. In this embodiment, the waist region 152C preferably enlarges in diameter by stretching of its sc material and thereby changing the relative angles of the nc braid fibers.

The bulb regions 162A, 162B can be formed from a nc material without a braid. Alternately, a sc material can be used with a braid. In either construction, the bulb regions 162A, 162B preferably inflate easily at low pressures and should reach the final bulb diameter at relatively low pressures below about 0.5 atm.

As this balloon 162 is inflated, the bevel regions 162D expand outwards to effectively "move" the regions 162D towards the center of the central waist region 162E. This new shape for the bevel regions 162D is formed and is controlled by the expanding braid and also is controlled by the shape of the material used to form the bevel regions. The braid fibers used in the waist 162C can be formed from Dacron, or other plastic monofilament fiber, or multifilament fiber, or metal monofilament fiber or multifilament metal fiber.

The manufacture of the balloon 162' in FIG. 7B may include a braided material that is embedded or attached to the waist 162C. In the initial, relatively low pressure configuration shown in FIG. 7B, the central waist 162E initially expands to a relatively small diameter which can be achieved by increasing the axially configuration or orientation of the braid angle. The waist can have a significantly smaller central waist diameter, $D_{W}$, than its final central waist diameter, $D_{W}$, as shown in FIG. 7C.

The beveled regions 162D are also preferably formed from a sc material with attached or embedded braided fibers. As the balloon 162' is inflated, the central waist 162E and beveled regions 162D expand outward until the braid angle becomes generally circumferentially oriented, thereby stopping the outward expansion. Also, upon inflation of the balloon 162' to its final configuration, the central waist 162E may shorten in length due to the presence of the attached braid. The bevel regions 162D expand outward in diameter relative to the central waist region 162E due to a different braid configuration. As the bevel braid angle becomes more circumferentially oriented in the final configuration, expansion become restricted.

The bulb regions 162A, 162B are preferably formed of a nc material that attains the final bulb diameter at a relatively low pressure below 0.5 atm. Other materials are contemplated and can also be used for the bulb material including a braided sc material that is formed at a diameter that is similar in its initial low pressure configuration to the final higher pressure configuration. As the balloon 162' is inflated, the waist length will reduce in length as the bevel regions 162E migrate closer to the central waist 162E as shown in FIG. 7C.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A balloon valvuloplasty catheter comprising:
a balloon disposed at a distal end of an elongated shaft;
a non-compliant distal bulb of said balloon having a fully inflated distal bulb diameter at a fully inflated distal bulb pressure of zero to 0.5 atm; said non-compliant distal bulb consisting solely of non-compliant material;
a semi-compliant proximal bulb having a smaller diameter than said distal bulb diameter at said fully inflated distal bulb pressure;
a waist portion of said balloon positioned between said distal bulb and said proximal bulb; said waist portion having a fully inflated waist diameter that is smaller than said fully inflated distal bulb diameter at said fully inflated distal bulb pressure;
said proximal bulb having a fully inflated proximal bulb diameter at a pressure higher than said fully inflated distal bulb pressure;
said fully inflated waist diameter is smaller than said fully inflated proximal bulb diameter at a pressure higher than said fully inflated distal bulb pressure.

2. The balloon catheter of claim 1, wherein said waist portion is between 4-10 mm in length.

3. The balloon catheter of claim 1, wherein said proximal bulb has a diameter that is smaller than a diameter of said waist portion and a diameter of said distal bulb at a pressure of 0.1 to 1.0 atm.

4. The balloon catheter of claim 1, wherein said balloon forms a dogbone structure wherein said fully inflated waist diameter is smaller than said fully inflated proximal bulb diameter of said proximal bulb.

5. The balloon catheter of claim 1, for dilation of valve leaflets attached at their base to an annulus wherein said fully inflated waist diameter is from 1 to 3 mm smaller than the diameter of the annulus.

6. The balloon catheter of claim 1, wherein said semi-compliant proximal bulb is formed from a polymer including the material of polyurethane, silicone copolymers, or high compliance Nylon.

7. The balloon catheter of claim 1, wherein said non-compliant distal bulb is formed from a non-compliant polymer having less compliance than said semi-compliant proximal bulb, said non-compliant distal bulb formed from a non-compliant polymer including polyethylene therephthalate, low compliance Nylon, low compliance Pebax, and other low compliance polymer materials used in low compliance medical device balloons.

8. The balloon catheter of claim 1, wherein said proximal bulb further comprises non-compliant fibers attached to said semi-compliant material to provide a limit said fully inflated proximal diameter.

9. The balloon catheter of claim 1, wherein said waist portion comprises a non-compliant material.

10. The balloon catheter of claim 1, wherein said waist portion comprises a semi-compliant material.

11. The balloon catheter of claim 10, wherein said waist portion further comprises non-compliant fibers attached to said waist semi-compliant material.

12. The balloon catheter of claim 10 wherein said semi-compliant material of said waist portion is able to expand under increasing pressure and volume into contact with a valve annulus resulting in an inflection point in a plot of pressure versus volume.

13. The balloon catheter of claim 1, wherein said fully inflated waist diameter is 1-8 mm smaller than said fully inflated distal bulb diameter and said fully inflated proximal bulb diameter.

14. The balloon catheter of claim 1, wherein at least a portion of said balloon is formed from a coextrusion of a non-compliant polymer layer over a semi-compliant polymer layer, and said non-compliant polymer layer has been removed from the semi-compliant proximal portion.

15. The balloon catheter of claim 1, wherein said waist has a fully inflated waist diameter range of 16-26 mm.

16. The balloon catheter of claim 1, wherein said distal bulb has a fully inflated distal bulb diameter range of 20-30 mm.

17. The balloon catheter of claim 1, wherein said proximal bulb has a proximal bulb diameter range of 5-18 mm at a pressure of 0.2-0.5 atm.

18. A balloon valvuloplasty catheter comprising:
a balloon disposed at a distal end of an elongated shaft;
a proximal portion of said balloon comprising a semi-compliant material that unfolds to form a first diameter at zero pressure and is capable of expansion to a larger second diameter under increasing pressure;
a non-compliant distal portion of said balloon; said non-compliant distal portion adapted to form a fully inflated distal diameter at a pressure of zero atm and comprising a non-compliant material, said distal portion being less compliant than said proximal portion, said distal portion having a larger diameter than said first diameter of said proximal portion at said zero pressure said distal portion consisting solely of non-compliant material;
a waist portion located between said proximal portion and said distal portion of said balloon comprising a semi-compliant material and having a fully inflated waist diameter that is smaller than said fully inflated distal diameter and smaller than said second larger diameter of said proximal portion;
wherein said proximal portion expands to a fully inflated proximal diameter at a higher pressure than said non-compliant distal portion expands to said fully inflated distal diameter.

19. The balloon catheter of claim 18, wherein said waist portion further comprises a plurality of fibers braided to restrict expansion of said waist portion to said fully inflated diameter.

* * * * *